US00PP22485P2

(12) United States Plant Patent
Korlipara

(10) Patent No.: US PP22,485 P2
(45) Date of Patent: Feb. 7, 2012

(54) ***COREOPSIS* PLANT NAMED 'GARNET'**

(50) Latin Name: ***Coreopsis* spp.**
Varietal Denomination: Garnet

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,261

(22) Filed: Nov. 9, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — Annette Para
(74) *Attorney, Agent, or Firm* — Klarquist Sparkman, LLP

(57) ABSTRACT

A new and distinct *Coreopsis* plant named 'Garnet' characterized by daisy-type flowers that grow to 4.5 cm in diameter, flowers that are deep rose with a darker center, grass green foliage on short stems, flowering for the whole summer, a dense, compact, mounding habit, and excellent vigor.

1 Drawing Sheet

Botanical denomination: *Coreopsis* spp.
Variety designation: 'Garnet'.
Parentage: (*Coreopsis* 'Heaven's Gate'×unknown).

BACKGROUND OF THE INVENTION

The present invention relates to a new and distinct *Coreopsis* and given the cultivar name 'Garnet'. *Coreopsis* is in the family Asteraceae. This new cultivar originated from an open pollinated cross of *Coreopsis* 'Heaven's Gate' (U.S. Plant Pat. No. 16,016) as the seed parent and an unknown proprietary *Coreopsis* as the pollen parent.

Compared to the seed parent, *Coreopsis* 'Heaven's Gate' (U.S. Plant Pat. No. 16,016), the new cultivar has flowers that are deep rose with a dark center rather than pink with a dark center and the habit is much smaller and tighter.

Compared to *Coreopsis* 'Limerock Ruby' (U.S. Plant Pat. No. 15,455), the new variety has flowers that are deep rose with a dark center rather that ruby red. The habit is shorter and more compact.

SUMMARY OF THE INVENTION

The following traits have been repeatedly observed and are determined to be the unique characteristics of the new variety. These characteristics in combination distinguish *Coreopsis* 'Garnet' as a new and distinct cultivar:

1. daisy-type flowers that grow to 4.5 cm in diameter,
2. flowers that are deep rose with a darker center,
3. grass green foliage on short stems,
4. flowering for the whole summer,
5. a dense, compact, mounding habit, and
6. excellent vigor.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one-year-old *Coreopsis* 'Garnet' growing in the ground in the trial field in August in Canby, Oreg.

DETAILED PLANT DESCRIPTION

The following is a detailed description of the new *Coreopsis* cultivar based on observations of four-month-old specimens growing in a 1 gallon pots in a warm greenhouse in May in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5$^{th}$ edition.

Plant:

*Type.*—Herbaceous perennial.
*Hardiness.*—USDA Zones 6 to 9.
*Size.*—29 cm wide and 35 cm tall to top of inflorescences.
*Form.*—Mound.
*Vigor.*—Excellent.
*Roots.*—Fibrous, stems root easily from stem cuttings.

Stem:

*Type.*—Ascending.
*Size.*—18 cm tall to where branches for flowering and 3 mm wide.
*Number of stems from the crown.*—2 to 5.
*Internode length.*—2 cm to 5 cm.
*Surface.*—Glabrous.
*Color.*—Green 137B.

Leaf:

*Type.*—Simple.
*Shape.*—Lanceolate to linear.
*Arrangement.*—Opposite.

*Size.*—Grows to 6 cm long and 1 cm wide.

*Apex.*—Obtuse.

*Margins.*—Entire.

*Petiole.*—Grows to 1.5 cm long and 1 wide, glabrous, Green 137B.

*Surface texture.*—Glabrous on top and bottom sides.

*Venation.*—Pinnate.

*Color.*—Topside Green N137C, bottom side Green 137B.

Inflorescence:

*Type.*—Long stalked terminal heads of daisy type inflorescences.

*Peduncle.*—Grows to 10.5 cm long, 1 mm wide, glabrous, Green 137B.

*Size.*—Grows to 4.5 cm wide and 8 mm deep.

*Immature.*—Globular, 6 mm wide and 5 mm deep, Green 137B on the bottom half to Greyed Orange 163A on the sides to Greyed Purple 187A on top, glabrous.

*Receptacle.*—Disc shaped, 2 mm wide and 1 mm deep, Green N137A.

*Phyllaries.*—In 2 series; first series closet to ray florets 4 mm deep and 12 mm wide, 8 in number, each 7 mm long and 5 mm wide, ovate, margin entire, tip acute, glabrous on both sides, from Green 137C at the base to Yellow Orange 23A to Greyed Purple 187B at the tip; lower series in an area 2 mm deep and 7 mm wide, 5 in number, 3 mm long and 2 mm wide, each ovate, margin entire, tip acute, both sides glabrous and Green 137A.

*Lastingness.*—Each inflorescence lasts about a week on the plant.

Florets:

*Type.*—Composite.

*Ray florets.*—8 in number with no pistil or stamen, grows to 19 mm long, 14 mm wide, obovate, with the tip three-lobed with lobe tips obtuse and the central lobe the longest, sometimes notched, margins entire, base attenuate, glabrous on both sides; topside Red Purple 72A with the base Greyed Purple 187A, bottom side closest to Purple N77B.

*Disc.*—Conic, deeper with maturity, 7 mm wide and becoming 4 mm deep with maturity, Purple N79A.

*Disc florets.*—Tubular, with stamen and pistil, about 75 in number, 7 mm long and 1 mm wide, tubular; corolla 3 mm long, tube Yellow Orange 17B, lobes Purple N79A; pistil 1, 5 mm long, ovary 1.5 mm long, Green White 157A, style and stigma 4 mm long, stigma extruding, 2-branched, stigma and style Yellow Orange 23A; stamen 5, anthers 1.5 mm long, Greyed Purple N186A, pollen Orange 23A.

*Bloom period.*—June through September in Canby, Oreg.

*Fragrance.*—Light, Chrysanthemum-like.

*Seed.*—None seen.

*Fertility.*—Sterile.

Disease and pests: *Coreopsis* are susceptible to mildew and fungal spots. No resistance is known for this variety. No problems have been seen in Canby, Oreg.

I claim:

1. A new and distinct *Coreopsis* plant as herein illustrated and described.

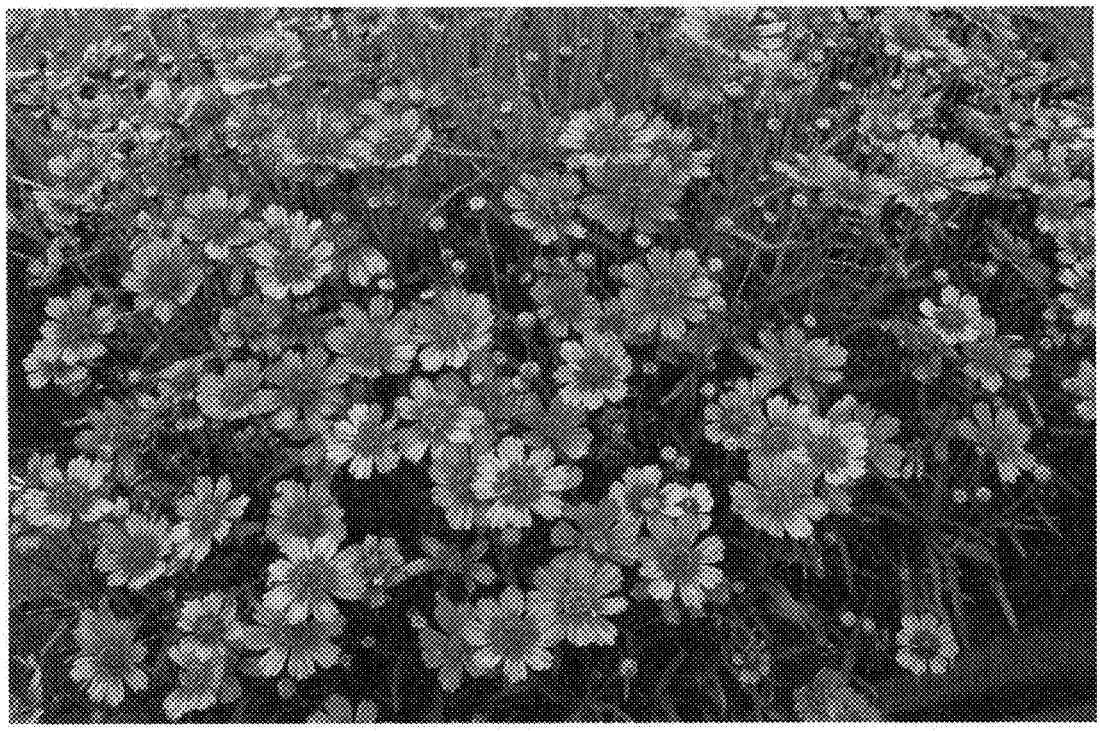

* * * * *